(12) United States Patent
Kiassos

(10) Patent No.: US 8,840,934 B2
(45) Date of Patent: Sep. 23, 2014

(54) USES OF AMMONIUM CHLORIDE

(75) Inventor: Diamantis Kiassos, Luxembourg (LU)

(73) Assignee: Rainbow Pharmaceutical SA, Luxembourg (LU)

(*) Notice: Subject to any disclaimer, the term of this patent is extended or adjusted under 35 U.S.C. 154(b) by 292 days.

(21) Appl. No.: 12/348,220

(22) Filed: Jan. 2, 2009

(65) Prior Publication Data
US 2010/0173020 A1 Jul. 8, 2010

(51) Int. Cl.
| A61K 33/00 | (2006.01) |
| A61P 31/12 | (2006.01) |
| A61P 35/00 | (2006.01) |
| A61P 37/00 | (2006.01) |
| A61K 33/02 | (2006.01) |
| A61J 1/03 | (2006.01) |
| A61J 7/04 | (2006.01) |
| A61K 33/14 | (2006.01) |

(52) U.S. Cl.
CPC ......... *A61K 33/02* (2013.01); *A61K 33/14* (2013.01); *A61J 1/035* (2013.01); *A61J 7/04* (2013.01)
USPC ............ 424/720; 424/400; 424/455; 424/464

(58) Field of Classification Search
USPC ................... 424/720, 400, 455, 464
See application file for complete search history.

(56) References Cited

U.S. PATENT DOCUMENTS

| 4,346,082 A | 8/1982 | Revici |
| 5,275,828 A * | 1/1994 | Hooper ............... 424/670 |
| 2002/0098242 A1 | 7/2002 | Darder ............... 424/490 |
| 2003/0162732 A1* | 8/2003 | Weidner ............... 514/42 |
| 2007/0251852 A1 | 11/2007 | Purdy et al. ............... 206/538 |
| 2007/0275060 A1 | 11/2007 | Befumo et al. ............... 424/468 |

FOREIGN PATENT DOCUMENTS

| EP | 0095833 | 12/1983 |
| EP | 0167191 | 8/1986 |
| EP | 1875918 | 1/2008 |
| GB | 2224720 | 5/1990 |
| GR | 1003980 | 9/2002 |
| GR | 2002100405 | 5/2004 |
| MX | 9503783 | 3/1997 |
| WO | 93/16993 | 9/1993 |
| WO | 96/32952 | 10/1996 |
| WO | 99/03453 | 1/1999 |
| WO | 2006/021426 | 3/2006 |
| WO | 2007/011524 | 1/2007 |

OTHER PUBLICATIONS

Invitation to Pay Additional Fees and Partial International Search Report for PCT/EP2009/067993 dated Feb. 19, 2010.
European Search Report for EP application 06386019.1 dated Mar. 2, 2007.
Communication pursuant to Art 94(3) EPC issued by EPO for EP application 06386019.1 dated Jun. 5, 2009.
Noting of loss of rights pursuant to Rule 112(1) EPC issued by EPO for EP application 06386019.1 dated Jan. 19, 2010.
Decision on request for further processing under Rule 135(3) EPC issued by EPO for EP application 06386019.1 dated Apr. 13, 2010.
International Search Report for PCT/EP2009/067993 dated Apr. 28, 2010.
Shin, Wan Yung et al., Ammonium Chloride Tolerance Tests in Rabbits Intravenously Administered with Multiple Doses of Carbon Tetrachloride Gorye Daihan-Yo Jabji—Korea University Medical Journal, Koryo Taehakkyo Uigwa Tachak, Seoul, KR, vol. 9, No. 1, 1972, pp. 113-123, Abstract.
Superti, Fabiana et al., The Effect of Lipophilic amines on the Growth of Hepatitis A virus in Frp/3 ells, Archives of Virology, New York, NY, US, vol. 96, No. 3-4, 1987, pp. 289-296, Abstract.
EP Office Action for application serial No. EP 06 386 019.1 filed on Jul. 3, 2006 in the name of Rainbow Pharmaceutical SA. Mail Date: May 3, 2011.
PCT Written Opinion for International application No. PCT/EP2009/067993 filed on Dec. 29, 2009 in the name of Rainbow Pharmaceutical SA. Mail Date: Apr. 28, 2010.
Hsu, M., et al., Hepatitis C virus glycoproteins mediate pH-dependent cell entry of pseudotyped retroviral particles, PNAS 2003, 100: 7271-7276.

* cited by examiner

*Primary Examiner* — Mina Haghighatian
(74) *Attorney, Agent, or Firm* — Steinfl & Bruno LLP

(57) ABSTRACT

A method to treat a condition in a patient comprising administering to the patient a therapeutically effective amount of a $NH_4Cl$ dosage form, a method for stimulating endogenous interferon production, and related methods, systems and dosage form housings.

29 Claims, 1 Drawing Sheet

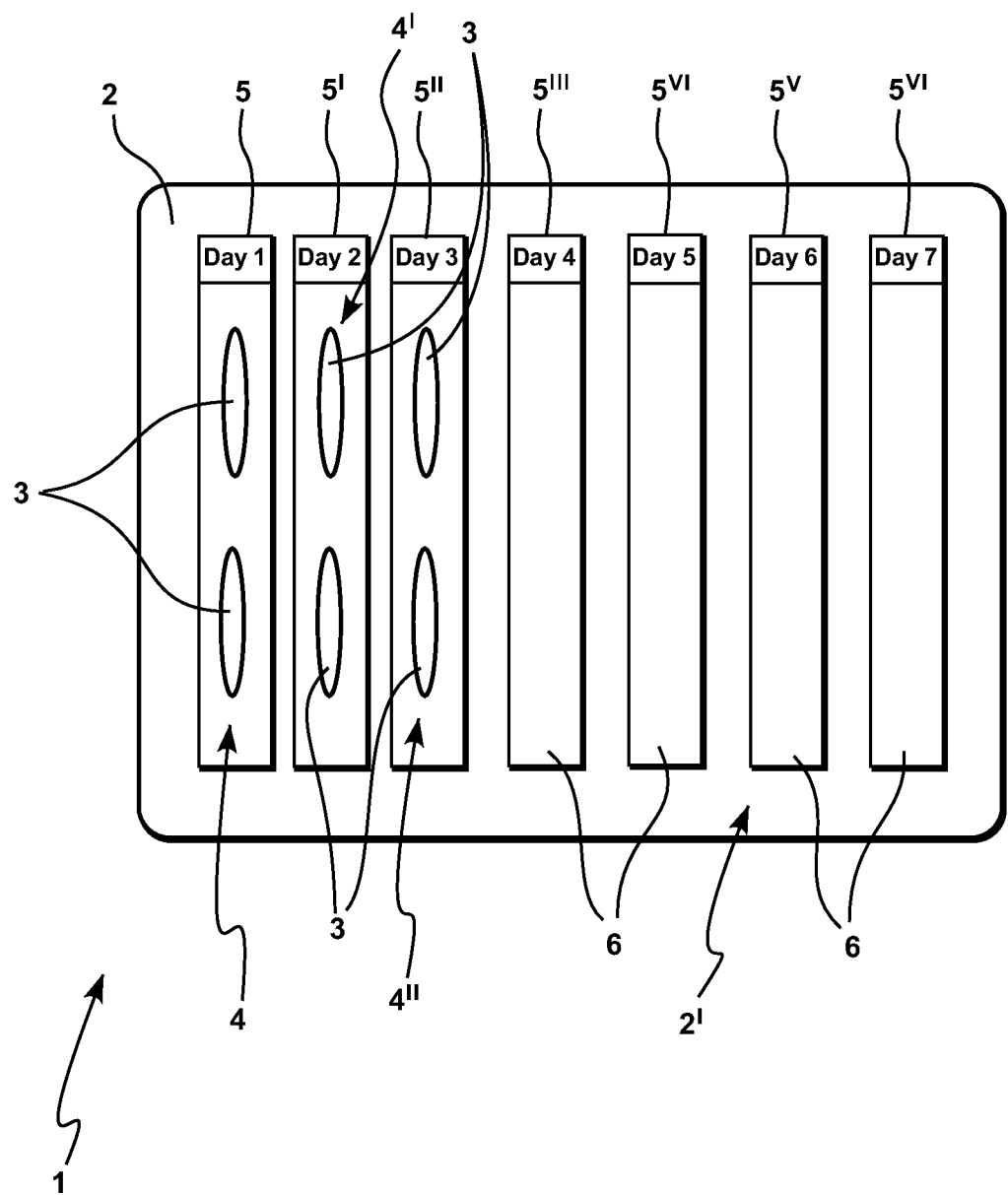

USES OF AMMONIUM CHLORIDE

CROSS REFERENCE TO RELATED APPLICATIONS

The present application is related to European patent publication EP1875918A2 entitled "New use of ammonium chloride for the therapy of total or partial hepatic failure and necrosis" published on Jan. 9, 2008, herein incorporated by reference in its entirety.

FIELD

The present disclosure relates to hepatic conditions, viral infections, and to conditions caused by toxic agents or autoimmune reactions. The present disclosure also relates to interferons, and to conditions treatable with interferons.

BACKGROUND

There are numerous pathological and toxic conditions that lead to a degenerative malfunction of the liver. Among these are hepatitis C (one-third of the infected patients evolve to hepatic cirrhosis), chronic hepatitis B and D, autoimmune hepatitis, non-alcoholic steatohepatitis, sclerosant cholangitis, Wilson's disease, Epstein-Barr virus infection and liver carcinoma.

As regards toxic conditions, the most common and relevant one is the one that occurs due to abuse of alcohol. Other toxic conditions are due to drugs and chemical hepatotoxic agents that may lead to hepatic necrosis, such as the poison of certain mushrooms (for example, Amanita falloides).

In conditions, when a large part of the hepatic parenchyma gets necrotized, the hepatic function decreases and may quickly lead to the death of the patient.

Nowadays there are no special treatments able to solve the hepatic necrosis problem and the patients that suffer from these degenerative diseases have a limited prognosis in relation to the survival time.

Interferons are used to treat several conditions affecting the liver as well as other conditions, including viral infections and other diseases, such as tumors.

SUMMARY

Provided herein are methods for treating or preventing hepatic conditions and/or various other conditions and related methods, systems and dosage form housing.

According to a first aspect, a method of treating or preventing a condition is disclosed, the condition being a hepatic condition, a viral infection, a condition caused by toxic agents or an autoimmune reaction, and/or a condition treatable by an interferon in a patient. The method comprises administering to the patient a therapeutically effective amount of a $NH_4Cl$ dosage form.

According to a second aspect a dosage form is disclosed, the dosage form comprising a pharmaceutically effective amount of $NH_4Cl$ and pharmaceutically acceptable excipients. In the dosage form the pharmaceutically effective amount of $NH_4Cl$ and pharmaceutically acceptable excipients are comprised in a gastric-resistant slow-release formulation. Furthermore the dosage form contains from 330 mg to 1500 mg of $NH_4Cl$.

According to a third aspect, a dosage form housing is described. The dosage form housing comprises a sheet of plastic material comprising a plurality of molded cavities protruding out of a face of the sheet, and presenting a carved, open side on an opposite face of the sheet. In the dosage form housing, the dimension of the cavities is usually sufficient to house one to three tablets or capsules of a $NH_4Cl$ dosage form. Additionally, in the dosage form housing, the sheet is coated with an aluminum film or a film of a material that can be ruptured by pressing the cavities from the upper side thereof, with the open side of the cavities closed by said film. In the dosage form housing, at least six of the cavities are arranged in three couples of cavities put side by side, each couple of cavities being associated with informational matter associated to said couples of cavities on a same face of the sheet wherein said cavities protrude. In the dosage form housing, the sheet is configured to present a substantial part thereof free from cavities, said substantial part being also associated with informational matter arranged side by side similarly to the informational matter associated to the couples of cavities. In the dosage form housing, both said informational matter associated to the couples of cavities and said informational matter associated to a part of the sheet free from cavities report a numerical, alphabetical or nominal indication of the days of the week.

According to a fourth aspect a method to stimulate release of an endogenous interferon in an individual is disclosed. The method comprises administering to the individual an effective amount of a $NH_4Cl$ dosage form.

The products, methods and systems herein described can be applied in several fields including basic biology research, applied biology, medical research, medical diagnostics, and therapeutics.

The details of one or more embodiments of the disclosure are set forth in the accompanying drawing and the description below. Other features, objects, and advantages will be apparent from the description and drawings, and from the appended claims.

BRIEF DESCRIPTION OF THE DRAWINGS

The accompanying drawing which is incorporated into and constitutes a part of this specification, illustrates one or more embodiments of the present disclosure and, together with the detailed description and the examples, serves to explain principles and implementations of the disclosure.

FIG. 1 shows a dosage form housing according to an embodiment herein disclosed.

DETAILED DESCRIPTION

Provided herein are products, methods and systems based on the administration of $NH_4Cl$ to a patient.

$NH_4Cl$ is a water-soluble inorganic salt, which is used for the treatment of hypochloremic metabolic alkalosis. It is also used for diagnostic purposes. It is administered up to a 15 N concentration, so that, through the isotopic ammonia and urea analysis of the urine of the patient, it is possible to evaluate the hepatic function.

In the Greek patent no. 1003980 and in Greek patent application no. 2002100405, a mechanism by which $NH_4Cl$ decreases the levels of bilirubin in patients with severe hepatic malfunctions and hepatic encephalopathy is described, which is caused by the increase of the bilirubin levels. These levels may be decreased by treatment with $NH_4Cl$. The treatment of liver malignant neoplasms is also described. $NH_4Cl$ salt is administered at a dosage of 600 mg/kg daily. No evidence of activity in human subjects is reported.

While working on an experimental study on Quinster rats which suffered from acute hepatitis caused with the known method of TAA administration, the Applicants found that the histological samples of the liver of the rats that had been administered $NH_4Cl$ had less necrosis signs than the ones of the placebo treatment. The Applicants noticed a partial or complete regeneration of the hepatic parenchyma. Furthermore, the Applicants noticed a decrease of the TNF-α (Tumor Necrosis Factor alfa) levels, while the levels of IL-6 were increased.

The levels of hyaluronic acid in patients with high-grade hepatic damage are usually high, but they appeared decreased in the treated Quinster rats. Furthermore, additional biochemical factors appeared improved.

It has thus been surprisingly found that $NH_4Cl$, when administered in vivo, is able to stimulate the release of endogenous interferons, as illustrated by the experiments exemplified in Example 1.

Interferons are a family of endogenous modulators of immune response. Interleukin IL-6 is also known as interferon beta-2. Interferons are very important in the treatment of RNA virus infections. Interferons are known to display antiviral, antiseptic and anticancer properties when administered as a drug.

More than 50% of hepatitis C patients treated with interferon respond with viral elimination (sustained virological response), better blood tests and better liver histology (detected on biopsy). There is some evidence that administering interferon immediately following infection can prevent chronic hepatitis C. However, patients infected by HCV often do not display symptoms until months or years after infection and this makes early treatment difficult.

Moreover, in case the infection is caused by Hepatitis C virus genotype 1, around 70% of patients is not responding to the interferon therapy.

Interferons (interferon beta-1a and interferon beta-1b) are also used in the treatment and control of multiple sclerosis, an autoimmune disorder.

Interferon is also used as a treatment for some types of cancer. It is used to treat cancer of the kidney, malignant melanoma and carcinoid tumours. It is also used sometimes to treat certain types of lymphoma and leukaemia.

Stimulation of endogenous interferons represents a substantial improvement with respect to the administration of interferons to a patient, as it is devoid of side effects that are often encountered in interferon therapy. Moreover, the effect of endogenous interferons is more prolonged over time. Additionally interferon therapy can be very expensive, while the present stimulation of endogenous interferons by administration of $NH_4Cl$ is cheap and safe.

The Applicants also surprisingly found that the administration of $NH_4Cl$ according to a particular protocol as described below to human patients affected by various forms of hepatitis virus is able to improve the patient's conditions and to drop the viral charge.

Administration of $NH_4Cl$ to a human is however accompanied by some side effects that may limit its use.

The most common side effects of the $NH_4Cl$ administration are metabolic oxidation, which is due to increased chlorides and the irritation of the gastric mucosa.

The first side effect is successfully overcome by the administration of a dose of from 2 to 5 gr of $NH_4Cl$ for from 3 to 5 days, with an interval of 4 to 2 days, respectively, without treatment. In another embodiment 2.8 to 3.5 gr of $NH_4Cl$ are administered for from 3 to 5 days, with an interval of 4 to 2 days, respectively, without treatment.

In still another embodiment about 3 gr of $NH_4Cl$ are administered with the same protocol reported above. In a still different embodiment, the protocol comprises 3 days of treatment with $NH_4Cl$ and 4 days of wash-out. The above protocol of administration can be repeated several times until the completion of the treatment as judged by the clinician. For example, 21 cycles of treatment are performed, which complies with the natural time of regeneration of liver after a partial hepatectomy in patients. Therefore, the duration of the treatment can be from 1 to 6 months or from 3 to 4 months for patients with partial necrosis.

Exemplary treatments based on the administration of NH4Cl to patients are exemplified in the illustration of Example 2.

In some embodiments, the irritation of the gastric mucosa is overcome by the enclosure of $NH_4Cl$ in gastro-resistant capsules or water-soluble acid resistant envelopes.

As said above, the dosage varies between 2 and 5 gr and the dosage form is preferably for oral administration in the form of granules or microcapsules with polymer compounds for the protection of the stomach.

In general, the formulation of the disclosure can be prepared according to standard techniques, as the ones reported in Remington's Pharmaceutical Sciences Handbook, Mack Pub. Co., N.Y., USA, 17th edition, 1985.

In order to assure a more constant blood concentration of $NH_4Cl$ after administration, the tablets, capsules or granules can be filled with a polymer or the matrix of a pharmaceutical form can be made of an excipient that slows the release of active ingredient in the gastrointestinal lumen.

In one embodiment, gastro-resistant granules or microcapsules in a ready to use suspension may be used. An exemplary gastro-resistant retard formulation is illustrated in Example 3.

In some embodiments, to assist the patient in the assumption of the drug according to the therapy protocol described above, it is also provided a dosage form housing, particularly a blister, as the one exemplary shown in FIG. 1.

In the illustration of FIG. 1, the dosage form housing 1 comprises a sheet 2 of plastic material wherein a plurality of cavities 3 are molded and protrude out of the plane of the sheet 2, while presenting a carved, open side on the opposite face thereof. The profile shape of such cavities 3, that in the FIGURE is elliptical, can vary and will take all the forms that can usually be adopted in this kind of applications. The dimension of the cavities 3 is sufficient to accommodate one to three tablets or capsules of $NH_4Cl$ formulated as said above. For example, each cavity 3 may contain three 500 mg tablets or one 1500 mg tablet of the drug, or any other dosage according to the dosage regimen indicated before.

The sheet 2, on the opposite side thereof (not shown in FIG. 1), is coated by the application of an aluminium film or a film of material that can be ruptured by pressing the cavities 3 from the upper side of the sheet 2. In such a way, the openings of the cavities 3 are closed by the said film.

The sheet 2 comprises six cavities 3, arranged in three couples 4, 4', 4" of cavities 3 put side by side. Each couple 4, 4', 4" is associated with an information matter 5, 5', 5", for example by printing or in any other way, on the same surface of the sheet 2 wherein the cavities 3 are raised.

The sheet 2 is large enough to present a substantial part 2' thereof without cavities 3. The said part 2' of the sheet 2 free from cavities 3 is also associated with information matter 5''', $5^{iv}$, $5^{v}$, $5^{vi}$ that is arranged side by side similarly to the information matter associated to the couples of cavities 3.

Specifically, both the said information matter 5, 5', 5" associated to the couples 4, 4', 4" of cavities 3 and the information matter 5''', $5^{iv}$, $5^{v}$, $5^{vi}$ associated to the part 2' of the sheet 2 that is free from cavities 3 report an indication of the days of the week, such as "day 1", "day 2" and so on or "Monday", "Wednesday" and so on or abbreviations thereof.

In such a way, only for three days a week the dosage form container 1 present cavities 3 filled with the drug, while the other days are free from drug according to the dosage regimen indicated above.

Moreover, for each day two cavities 3 are present, each containing, for example, a 1500 mg NH$_4$Cl dosage form (one or more tablets or capsules), one for a morning administration (typically before breakfast) and the other for an evening administration (typically before dinner).

In another embodiment, the said information matter $5'''$, $5^{iv}$, $5^v$, $5^{vi}$ associated to the part $2'$ of the sheet 2 that is free from cavities 3 is arranged on a strip 6 that can be torn off on the day of break of the treatment reported in the information matter.

In another embodiment, the sheet 2 may present seven couples of cavities 3, one for each day of a week, but only three couples will include the wanted dosage form, the other four couples of cavities 3 being empty. Instead of these latter four couples of cavities, only four single cavities may also be foreseen. These empty cavities are also designed to be pressed on the day of break of the treatment reported in the information matter.

According to what has been said above, it is provided a method of treating or preventing a viral infection, hepatic failure, hepatic necrosis and other conditions caused by toxic agents or by autoimmune reaction or a tumor that is susceptible of treatment with interferons alfa, beta or gamma, the method comprising administering a therapeutically effective amount of NH$_4$Cl dosage form to a patient in need thereof.

In particular, provided herein is a method for the pharmaceutical treatment of hepatic failure and necrosis, which is caused by various toxic agents. Provided herein are also methods for the treatment of viral infections or other diseases, specifically tumors, that can be treated with interferons and in particular with interferons alfa beta or gamma.

In some embodiments, the therapeutically effective amount is comprised between 2 and 5 gr a day.

In some embodiments, the therapeutically effective amount is comprised between 2.8 and 3.5 gr a day.

In some embodiments, the therapeutically effective amount is about 3 gr a day.

In some embodiments, administering to the patient a therapeutically effective amount of a NH$_4$Cl dosage form is performed by administering the NH$_4$Cl dosage form to the patient for from three to five days thus providing an NH$_4$Cl treatment to the patient, stopping the NH$_4$Cl treatment for from four to two days, respectively, thus completing a NH$_4$Cl treatment cycle and repeating the NH$_4$Cl treatment cycle for a treatment duration of from 1 to 6 months.

In some embodiments, administering to the patient a therapeutically effective amount of a NH$_4$Cl dosage form is performed by administering the NH$_4$Cl dosage form to the patient for three days, thus providing an NH$_4$Cl treatment to the patient, stopping the treatment for four days thus completing a NH$_4$Cl treatment cycle and repeating the NH$_4$Cl treatment cycle for a treatment duration of from 1 to 6 months.

In some embodiments, the condition is partial necrosis and the treatment duration is from 3 to 4 months.

In some embodiments, the viral infections will be those infections treatable with interferons alfa, beta or gamma. In some embodiments the viral infections are hepatitis B, hepatitis D, hepatitis C or chronic hepatitis C, D or B, or Epstein-Barr virus infection and in particular complicated Epstein Barr virus infection.

In some embodiments, conditions that can be treated according to the disclosure are selected from autoimmune hepatitis, non-alcoholic steatohepatitis, sclerosant cholangitis, multiple sclerosis, Wilson's disease and liver carcinoma.

In some embodiments, the toxic agents are selected from alcohol or drugs, with particular reference to the abuse thereof, chemical hepatotoxic agents, and in particular agents that may lead to hepatic necrosis, such as the poison of certain mushrooms (for example, Amanita falloides).

In some embodiments, the condition treatable with an interferon is a tumor. More particularly, the tumor can be selected from cancer of the kidney, malignant melanoma, carcinoid tumors, lymphoma and leukaemia.

In some embodiments, the NH$_4$Cl dosage form is a gastro-resistant pharmaceutical formulation.

In some embodiments, the NH$_4$Cl dosage form is a slow-release pharmaceutical formulation.

In some embodiments, the NH$_4$Cl dosage form is in the form of gastro-resistant granules or microcapsules in a ready to use suspension.

In some embodiments, the NH$_4$Cl dosage form comprises excipients selected from the group consisting of hydroxypropylmethylcellulose, polyvinylpyrrolidone, sodium croscarmellose, magnesium stearate, talc, and simeticone in a gastro-resistant retard formulation.

In some embodiments, the patient is a human.

In several embodiments, the treatment of the disclosure can also be associated with exogenously administered interferons or antiviral agents.

In some embodiments, the informational matter in the dosage form housing are associated to the part of the sheet that is free from cavities is arranged on a strip that can be torn off on the day of break of the treatment reported in the informational matter.

In some embodiments, a sheet in the dosage form housing exhibits seven couples of cavities, one for each day of a week, only three couples of cavities including said dosage form, the other four couples of cavities being empty, said empty cavities being also designed to be pressed on the day of break of the treatment reported in the informational matter.

In some embodiments, the four couples of empty cavities in the dosage form housing can be replaced by four single cavities.

Further details concerning the methods, systems, products and compositions herein described, and generally manufacturing and packaging of the compositions and housings, can be identified by the person skilled in the art upon reading of the present disclosure.

EXAMPLES

The products, methods and system herein disclosed are further illustrated in the following examples, which are provided by way of illustration and are not intended to be limiting.

Example 1

NH$_4$Cl Stimulates Release of Endogenous Interferons

Release of endogenous interferons was proven by the following "In vivo" experimental data on Quinster rats Thioacetamid (TAA) was given to adult male Quinster rats with a course of 400 mg TAA/kg B.W. every 24 hours and for 3 consecutive days. 2 hours after the $2^{nd}$ and $3^{rd}$ dose of TTA, the animals were treated per os either with ammonium chloride (300 or 600 or 900 mg/kg B.W.) or the same dose of water. The animals were sacrificed in 6 and 12 hours after the $3^{rd}$ treatment with TTA. TNF-α and IL-6 levels were measured in serum (ELISA test) after 12 hours post the third TAA injection and the results are reported in the following table.

| Group | IL-6 | TNF-α |
|---|---|---|
| Control | 11 ± 5 | 21 ± 4 |
| I | 58 ± 9 | 65 ± 15 |
| II | 69 ± 12 | 52 ± 17 |
| III | 92 ± 8 | 32 ± 6 |
| IV | 73 ± 12 | 45 ± 9 |

(Values represent pg/dL are expressed as mean ± SD; at least 8 animals per group)

These results indicate an increase of Interleukines following treatment of Quinster rats with $NH_4Cl$.

This evidence proves that endogeneous interferons, and in particular IL-6, are increased "in vivo" after treatment with $NH_4Cl$.

Example 2

Use of $NH_4Cl$ in Treating Hepatitis Virus

Clinical evidence related to administration of $NH_4Cl$ to individuals were provided as indicated below.

Patients were treated according to the above described protocol, using a dose of 3 gr/day. The clinical results are given below:

| Patient A Disease: chronic hepatitis B | |
|---|---|
| Viral charge before treatment: | $1.65 \times 10^6$ IU/ml |
| Viral charge after 3 months of treatment | $1.65 \times 10^3$ IU/ml |
| Patient B Disease: hepatitis C | |
| Viral charge before treatment | $1.65 \times 10^8$ IU/ml |
| Viral charge after 3 months of treatment | $1.65 \times 10^6$ IU/ml |

As shown by the above data, treatment with $NH_4Cl$ is able of reducing the viral charge of a factor of at least $10^2$ in humans.

Example 3

$NH_4Cl$ Gastro-Resistant Retard Tablet

A tablet for providing $NH_4Cl$ to an individual was formulated as indicated below.

The tablet is formulated according to standard techniques and contains 500 mg of $NH_4Cl$ and the following excipients: hydroxypropylmethylcellulose, polyvinylpyrrolidone, sodium croscarmellose, magnesium stearate, talc, simeticone.

Example of gastro-resistant retard tablet:

| Ammonium Chloride | mg | 500 |
|---|---|---|
| Hydroxypropylmethylcellulose | mg | 40 |
| Polyvinylpyrrolidone | mg | 60 |
| Sodium Croscarmellose | mg | 10 |
| Magnesium stearate | mg | 1 |
| Talc | mg | 120 |
| Simeticone | mg | 50 |

The tablets are coated by one or more layers, which are resistant to the gastric acids but dissolve into the intestine, and which guarantee a slow release of the active ingredient.

In summary, in some embodiments, the present disclosure relates to a method for treatment of hepatic failure and necrosis, which is caused by various toxic agents, and for the treatment of viral infections or other diseases, specifically tumors, that can be treated with interferons. More particularly, in some embodiments the present disclosure relates to a method of treating or preventing a viral infection, hepatic failure, hepatic necrosis or other conditions caused by toxic agents or by autoimmune reaction or a tumor that is susceptible of treatment with interferons alfa, beta or gamma, the method comprising administering a pharmaceutically effective amount of a $NH_4Cl$ dosage form together with pharmaceutically acceptable excipients to a patient in need thereof.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the products, methods and system of the present disclosure, exemplary appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A method of treating a hepatic condition, a viral infection, a condition caused by toxic agents or an autoimmune reaction, and/or a condition treatable by an interferon in a patient, the method consisting of:
   administering to the patient a therapeutically effective amount of $NH_4Cl$ ranging between 2.8 and 3.5 gr in an $NH_4Cl$ daily dosage form to treat a hepatic condition, a viral infection, a condition caused by toxic agents or an autoimmune reaction, and/or a condition treatable by an interferon in the patient,
   wherein the administering is performed in a treatment cycle comprising
      an administering time period of three days wherein administering the $NH_4Cl$ daily dosage form is performed; followed by
      an interval time period of four days wherein administering the $NH_4Cl$ daily dosage form is stopped;
   and wherein the $NH_4Cl$ daily dosage form consists of $NH_4Cl$ as an active ingredient.

2. A method of treating a hepatic condition, a viral infection, a condition caused by toxic agents or an autoimmune reaction, and/or a condition treatable by an interferon in a patient, the method comprising:
   administering to the patient a therapeutically effective amount of $NH_4Cl$ ranging between 2.8 and 3.5 gr in an $NH_4Cl$ daily dosage form to treat a hepatic condition, a viral infection, a condition caused by toxic agents or an autoimmune reaction, and/or a condition treatable by an interferon in the patient,
   wherein the administering is performed in a treatment cycle comprising
      an administering time period of three days wherein administering the $NH_4Cl$ daily dosage form is performed; followed by
      an interval time period of four days wherein administering the $NH_4Cl$ daily dosage form is stopped.

3. The method according to claim 1, wherein the therapeutically effective amount of $NH_4Cl$ in the $NH_4Cl$ daily dosage form is about 3 gr.

4. The method according to claim 1, wherein the condition is partial necrosis.

5. The method according to claim 1, wherein the viral infection is an infection treatable with interferons alfa, beta, and/or gamma.

6. The method according to claim 5, wherein the viral infection is selected from the group consisting of hepatitis B, hepatitis D, hepatitis C, chronic hepatitis C, chronic hepatitis D, chronic hepatitis B, and Eipstein-Barr virus infection.

7. The method according to claim 1, wherein the condition caused by a toxic agent or an autoimmune reaction is selected from the group consisting of autoimmune hepatitis, non-alcoholic steatohepatitis, sclerosing cholangitis, multiple sclerosis, Wilson's disease, and liver carcinoma.

8. The method according to claim 1, wherein the toxic agent is selected from group consisting of alcohol, drugs, chemical hepatotoxic agents, and mushroom poison.

9. The method according to claim 1, wherein the condition treatable by an interferon is a tumor, the tumor is selected from the group consisting of cancer of the kidney, malignant melanoma, carcinoid tumors, lymphoma, and leukemia.

10. The method according to claim 1, wherein the $NH_4Cl$ dosage form is a gastro-resistant pharmaceutical formulation.

11. The method according to claim 1, wherein the $NH_4Cl$ dosage form is a slow-release pharmaceutical formulation.

12. The method according to claim 1, wherein the $NH_4Cl$ dosage form is in a form of gastro-resistant granules or microcapsules in a ready to use suspension.

13. The method according to claim 1, wherein the $NH_4Cl$ dosage form comprises excipients selected from the group consisting of hydroxypropylmethylcellulose, polyvinylpyrrolidone, sodium croscarmellose, magnesium stearate, talc, and simethicone in a gastro-resistant retard formulation.

14. The method according to claim 1, wherein the patient is human.

15. A method for stimulating release of an endogenous interferon in an individual, the method comprising administering to the individual an effective amount of a $NH_4Cl$ in a $NH_4Cl$ daily dosage form to stimulate release of endogenous interferon in the individual, wherein the $NH_4Cl$ daily dosage form is administered according to the method of claim 1.

16. The method according to claim 2, wherein the therapeutically effective amount of $NH_4Cl$ in the $NH_4Cl$ daily dosage form is about 3 gr.

17. The method according to claim 2, wherein the treatment cycle is repeated for from 1 to 6 months.

18. The method according to claim 2, wherein the condition is partial necrosis and the treatment cycle is repeated for from 3 to 4 months.

19. The method according to claim 2, wherein the viral infections are infections treatable with interferons alfa, beta, and/or gamma.

20. The method according to claim 19, wherein the viral infection is selected from the group consisting of hepatitis B, hepatitis D, hepatitis C, chronic hepatitis C, chronic hepatitis D, chronic hepatitis B, and Eipstein-Barr virus infection.

21. The method according to claim 2, wherein the condition caused by a toxic agent or by an autoimmune reaction is selected from the group consisting of autoimmune hepatitis, non-alcoholic steatohepatitis, sclerosing cholangitis, multiple sclerosis, Wilson's disease and liver carcinoma.

22. The method according to claim 2, wherein the toxic agents are selected from group consisting of alcohol, drugs, chemical hepatotoxic agents, and mushroom poison.

23. The method according to claim 2, wherein the condition treatable by an interferon is a tumor, the tumor is selected from the group consisting of cancer of the kidney, malignant melanoma, carcinoid tumors, lymphoma and leukemia.

24. The method according to claim 2, wherein the $NH_4Cl$ dosage form is a gastro-resistant pharmaceutical formulation.

25. The method according to claim 2, wherein the $NH_4Cl$ dosage form is a slow-release pharmaceutical formulation.

26. The method according to claim 2, wherein the $NH_4Cl$ dosage form is in the form of gastro-resistant granules or microcapsules in a ready to use suspension.

27. The method according to claim 2, wherein the $NH_4Cl$ dosage form comprises excipients selected from the group consisting of hydroxypropylmethylcellulose, polyvinylpyrrolidone, sodium croscarmellose, magnesium stearate, talc, and simethicone in a gastro-resistant retard formulation.

28. The method according to claim 2, wherein the patient is a human.

29. A method for stimulating release of an endogenous interferon in an individual, the method comprising administering to the individual an effective amount of a $NH_4Cl$ in a $NH_4Cl$ daily dosage form to stimulate release of the endogenous interferon in the individual, wherein the $NH_4Cl$ daily dosage form is administered according to the method of claim 2.

* * * * *